US006395759B1

(12) United States Patent
Thompson et al.

(10) Patent No.: US 6,395,759 B1
(45) Date of Patent: May 28, 2002

(54) SUBSTITUTED BENZAMIDE DERIVATIVES AND PHARMACEUTICAL COMPOSITIONS CONTAINING THEM

(75) Inventors: Mervyn Thompson, Harlow; Antonio Kuok Keong Vong, Sawbridge; Robert William Ward, Great Dunmow, all of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/319,124

(22) PCT Filed: Dec. 1, 1997

(86) PCT No.: PCT/EP97/06949
§ 371 (c)(1),
(2), (4) Date: Jun. 1, 1999

(87) PCT Pub. No.: WO98/24764
PCT Pub. Date: Jun. 11, 1998

(51) Int. Cl.[7] .................... A61K 31/445; A61K 31/40; C07D 211/32; C07D 207/08
(52) U.S. Cl. .................... 514/331; 514/428; 546/234; 548/567
(58) Field of Search .................... 546/234; 548/567; 514/331, 428

(56) References Cited

U.S. PATENT DOCUMENTS 4,022,900 A 5/1977 Mathison .................... 424/258
5,358,948 A * 10/1994 Bradshaw et al. .......... 514/252

OTHER PUBLICATIONS

Leete, et al., "Biosynthesis of Shihunine in *Dendrobium pierardii*", (1976), Journal of the American Chemical Society, vol. 98, pp. 6321–6325 (XP002065496).
Makovec, et al., "Antiallergic and Cytoprotective Activity of New N–Phenylbenzamido Acid Derivatives", (1992), J. Med. Chem., vol. 35, pp. 3633–3640.
Meth–Cohn, et al., "Syntheses of Heterocyclic Compounds. Part IV. Oxidative Cyclisation of Aromatic Amines and their N–Acyl Derivatives", (1963), Journal of the American Chemical Society, vol. 83, pp. 4666–4669.

* cited by examiner

Primary Examiner—D. Margaret Seaman
Assistant Examiner—Raymond Covington
(74) Attorney, Agent, or Firm—Linda E. Hall; Charles M. Kinzig; William T. King

(57) ABSTRACT

Compounds of formula (I) and pharmaceutically acceptable salts thereof, where G is a methylene or ethylene linkage; $R^1$ is hydrogen, $C_{1-6}$alkylO—; $R^2$ is hydrogen, halogen, CN, $N_3$, trifluoromethyldiazirinyl, $CF_3$, $CF_3O$—, $CF_3S$—, $CF_3CO$—, $C_{1-6}$alkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylCO—, $C_{3-6}$cycloalkyl-$C_{1-4}$-alkylCO—, phenyl, phenoxy, benzyloxy, benzoyl and substituted benzoyl, phenyl-$C_{1-4}$alkyl-, $C_{1-6}$alkylSO$_2$—, $(C_{1-4}$alkyl$)_2$NSO$_2$— or $(C_{1-4}$alkyl$)$NHSO$_2$—; $R^3$ is hydrogen, halogen, CN, $N_3$, trifluoromethyldiazirinyl, $C_{1-6}$alkylO—, $C_{1-6}$alkylS—, $C_{1-6}$alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO$—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, or —NR$^5$R$^6$ where $R^5$ is hydrogen or $C_{1-4}$alkyl; and $R^6$ is hydrogen, $C_{1-4}$alkyl, —CHO, —CO$_2$C$_{1-4}$alkyl or —COC$_{1-4}$alkyl; $R^4$ is hydrogen, $C_{1-6}$alkyl, $C_{1-6}$alkenyl, or $C_{1-6}$alkynyl, are useful in the prevention and treatment of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, etc.

(I)

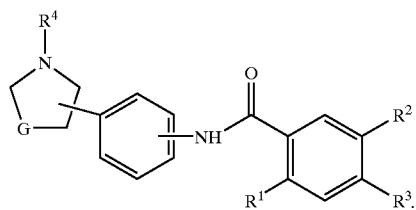

7 Claims, No Drawings

SUBSTITUTED BENZAMIDE DERIVATIVES AND PHARMACEUTICAL COMPOSITIONS CONTAINING THEM

This invention relates to novel compounds, to processes for preparing them, and to their use as therapeutic agents.

U.S. Pat. No. 4,022,900 (Marion) discloses benzamido-tetrahydroisoquinolines having anti-hypertensive and vasodilator properties, including the compound 2,4,5-trimethoxy-N-(2-methyl-1,2,3,4-tetrahydroisoquinolin-5-yl)benzamide.

The compound N-[2-(1-methyl-pyrrolidin-2-yl)-phenyl] benzamide is disclosed in JACS 1976, 98, p6321.

It has now been surprisingly found that benzamide compounds of formula (I) below possess anti-convulsant activity and are therefore believed to be useful in the treatment and/or prevention of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodys-thesias in diseases such as diabetes, MS and motor neurone disease, ataxias, muscular rigidity (spasticity), temporomandibular joint dysfunction, panic disorders and/or aggression.

Accordingly, the present invention provides a compound of formula (I) or pharmaceutically acceptable salt thereof.

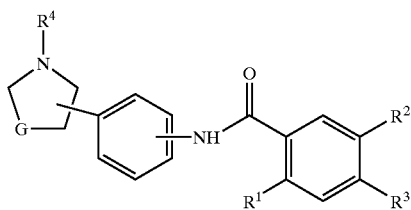

(I)

where

G is a methylene or ethylene linkage;

$R^1$ is hydrogen, $C_{1-6}$ alkylO—;

$R^2$ is hydrogen, halogen, CN, $N_3$, trifluoromethyldiazirinyl, $CF_3$, $CF_3O$—, $CF_3S$—, $CF_3CO$—, $C_{1-6}$alkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl and substituted benzoyl, phenyl-$C_{1-4}$alkyl-, $C_{1-6}$alkylSO$_2$—, ($C_{1-4}$alkyl)$_2$NSO$_2$— or ($C_{1-4}$alkyl)NHSO$_2$—;

$R^3$ is hydrogen, halogen, CN, $N_3$, trifluoromethyldiazirinyl, $C_{1-6}$ alkylO—, $C_{1-6}$ alkylS—, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO$—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, or —NR$^5$R$^6$ where R$^5$ is hydrogen or $C_{1-4}$ alkyl, and $R^6$ is hydrogen, $C_{1-4}$alkyl, —CHO, —CO$_2$C$_{1-4}$alkyl or —COC$_{1-4}$alkyl;

$R^4$ is hydrogen, $C_{1-6}$ alkyl, $C_{1-6}$ alkenyl, or $C_{1-6}$ alkynyl.

The compounds of this invention are typically (2-pyrrolidin/2-piperidin-yl-phenyl)-benzamides.

In the formula (I), groups are typically based on straight chain alkyl groups, but in general alkyl groups may be straight chain or branched.

Suitable $C_{3-6}$ cycloalkyl groups include cyclopropyl, cyclobutyl, cyclopentyl, and cyclohexyl. Further, it should be appreciated that whenever the term phenyl is mentioned above, the phenyl moiety is optionally substitued for example it is independently substituted one or more times by a substituent selected from the list comprising halogen, $C_{1-6}$ alkyl, $C_{1-6}$ alkoxy, $C_{1-6}$ alkylcarbonyl.

Suitable halo substituents include fluoro, chloro, iodo and bromo.

A suitable group of compounds of formula (I) have $R^1$ as methoxy, ethoxy or n-propoxy $R^2$ as hydrogen, methoxy, bromo, chloro, iodo, acetyl, benzoyl, trifluoromethyl, trifluoroacetyl.

$R^3$ as hydrogen, methyl, ethyl, n-butyl, t-butyl, phenyl, methoxy, ethoxy, isopropoxy, n-butoxy, benzyloxy, amino, acetylamino, benzoyl, chloro or azido $R^4$ as hydrogen, methyl, ethyl or propyl.

Examples of compounds of formula (I) are:

2-[3-(4-tert-butyl-2-methoxy-benzoylamino)-phenyl]-pyrrolidine.

2-[3-(4-tert-butyl-2-methoxy-benzoylamino)-phenyl]-piperidine.

When synthesised, these compounds are often in salt form, typically the hydrochloride or trifluoroacetate, and such salts also form part of this invention. Such salts may be used in preparing pharmaceutically acceptable salts. The compounds and their salts may be obtained as solvates, such as hydrates, and these also form part of this invention. It should be appreciated that the present compounds possess a chiral centre, therefore the present invention extends to each enantiomer separately and to all mixtures of enantiomers including racemates.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual or transdermal administration.

An amount effective to treat the disorders hereinbefore described depends on the usual factors such as the nature and severity of the disorders being treated and the weight of the mammal. However, a unit dose will normally contain 1 to 5000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 5000 mg, for example 1 to 1500 mg, that is in the range of approximately 0.01 to 70 mg/kg/day, for example 0.1 to 20 mg/kg/day.

It is greatly preferred that the compound of formula (I) is administered in the form of a unit-dose composition, such as a unit dose oral, including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

The present invention further provides a pharmaceutical composition for use in the treatment and/or prevention of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigerninal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, panic disorders and/or aggression, which comprises a compound of formula (I), or a pharmaceutically acceptable salt or solvate thereof, and a pharmaceutically acceptable carrier.

The present invention also provides a method of treatment and/or prevention of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, panic disorders and/or aggression comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prevention of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, panic disorders and/or aggression.

In a further aspect the present invention provides a pharmaceutical composition containing a compound of formula (I), or a pharmaceutically acceptable salt or solvate thereof, and a pharmaceutically acceptable carrier.

In a further aspect the invention provides the use of a compound of formula (I), or a pharmaceutically acceptable salt or solvate thereof, as a therapeutic agent, in particular for the treatment and/or prevention of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimrer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, panic disorders and/or aggression.

Another aspect of the invention provides a process for the preparation of compounds of formula (I), which comprises reacting a compound of formula (II)

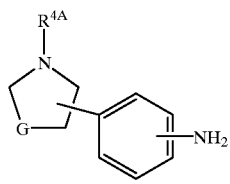

(II)

where G is as defined for formula (I) and $R^{4A}$ is $R^4$ as defined for formula (I) or a group convertible to $R^4$ or a protecting group with a compound of formula (III)

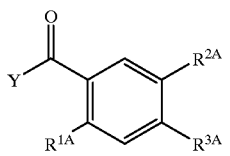

(III)

where Y is Cl or other halogen or OH, and $R^{1A}$, $R^{2A}$, and $R^{3A}$ are respectively $R^1$, $R^2$, and $R^3$ as defined for formula (I) or groups convertible to $R^1$, $R^2$, and $R^3$, and where required converting a $R^{1A}$, $R^{2A}$, $R^{3A}$ or $R^{4A}$ group to a $R^1$, $R^2$, $R^3$ or $R^4$ group, converting one $R^1$, $R^2$, $R^3$ or $R^4$ group to another $R^1$, $R^2$, $R^3$ or $R^4$ group, converting a hydrochloride salt product to the free base or another pharmaceutically acceptable salt, or converting a free base product to a pharmaceutically acceptable salt.

Reaction of a compound of formula (III) which is a benzoyl chloride derivative Y=Cl) will lead directly to the hydrochloride salt. Suitable solvents include dichloromethane and ethyl acetate. A base such as triethylamine may be used. When the compound of formula (III) is a benzoic acid derivative (Y=OH), conventional conditions for condensation of aromatic acids with amines may be used, for example reacting the components in a mixture of 1-ethyl-3-(3-dimethylaminopropyl)- carbodiimide, hydroxybenzotriazole in a solvent such as dimethylformamide.

Conversions of an $R^{1A}$, $R^{2A}$, $R^{3A}$ or $R^{4A}$ group to a $R^1$, $R^2$, $R^3$ or $R^4$ group typically arise when a protecting group is needed during the above coupling reaction or during the preparation of the reactants by the procedures described below. Interconversion of one $R^1$, $R^2$, $R^3$ or $R^4$ group to another typically arises when one compound of formula (I) is used as the immediate precursor of another compound of formula (I) or when it is easier to introduce a more complex or reactive substituent at the end of a synthetic sequence.

Compounds of formula (II) where G is methylene may be prepared from a compound of formula (IV)

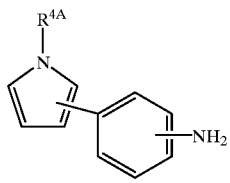

(IV)

by hydrogenation of the pyrrole ring, for example using hydrogen/platinum in a suitable solvent such as methanol at ambient temperature and pressure.

Compounds of formula (IV) may be prepared by reaction of a halo-aniline with a boronic acid derivative of a $R^{4A}$-substituted pyrrole (e.g. t-butyloxycarbonyl protected). Using $Na_2CO_3$/DME(dimethoxyethane)/H2O cat $Pd(PPh_3)_4$ as a palladium (o) catalyst. Or in the case of piperidine analogs 2-halopyridine (e.g. 2-bromopyridine) is coupled with a suitable aminophenyl boromic acid under similar conditions. Acylation (EDC, HOBT, DMF) with a compound of formula (III) followed by quaternisation with $R_4X$, where X is a leaving group such as halgen, for example iodine. Examples of $R_4X$ specifically include methyl iodide, which may be reacted in an inert organic solvent such as acetone followed by hydrogeneration using conventional conditions such as (Pt $O_c$, $H_2$, methanol) to give a compound of formula (I).

Compounds of formula (III) can be prepared by further substitution of commercially available benzoic acid derivatives using conventional procedures. Suitable starting materials are 2,4-dimethoxy benzoic acid, 2-methoxy 4-tert-butyl benzoic acid and 2-methoxy 4-chloro benzoic acid.

It should be appreciated that amines of formula (II) are suitably resolved using conventional technique before reacting with a compound of formula (III). Alternatively, compounds of formula (I) which are enantiomeric mixtures may be resolved using conventional techniques.

The preparation of compounds of this invention is further illustrated by the following Preparations and Examples. The utility of compounds of this invention is shown by the Pharmacological Data that follow the Examples.

Preparation 1

2-(3-Aminophenyl)-1-(tert-butyloxycarbonyl)-pyrrole

A mixture of 3-bromoaniline (0.48 g), N-tert-butyloxycarbonyl-2-pyrrole-boronic acid (0.6 g), sodium carbonate (0.91 g), tetrakis-(triphenylphosphine) palladium (1.3 g) in DME (30 mL) and water (5 mL) was heated under reflux under argon for 16 h. The reaction mixture was allowed to cool to room temperature and poured into water. It was then extracted with ethyl acetate. The organic layer was washed with brine, dried (sodium sulfate) and evaporated in vacuo. Repeated suction silica gel chromatography eluting with ethyl acetate in hexane (from 10% to 50%, 10% increments) gave desired product as an amber solid (0.3 g).

Mass Spectroscopy (API+) gave molecular ion peak at 259 as M+1.

Preparation 2

(±)-2-(3-Aminophenyl)-1-(tert-butyloxyearbonyl)-pyrrolidine

A solution of 2-(3-aminophenyl)-1-tert-butyloxycarbonyl)-pyrrole (0.3 g) in the presence of 5% platinum on carbon (0.03 g) in methanol (30 rnL) was allowed to stir under an atmosphere of hydrogen for 18 h. The reaction mixture was filtered through a pad of Kieselguhr and the filtrate evaporated in vacuo to dryness. Suction silica gel chromatography of the residue eluting with ethyl acetate followed by methanol/ethyl acetate (5% to 10%) gave the title compound as an amber oil (0.05 g).

$^1$H (250 MHz, CDCl$_3$): 1.22 and 1.45 (9H, 2 br. s); 1.85 and 2.25 (4H, 2 br. m); 3.6 (4H, br. s); 4.68 and 4.87 (1H, 2 br. s); 6.5 (3H, m); 7.07 (1H, t).

Preparation 3

(±)-2-[3-(4-tert-Butyl-2-methoxy-benzoylamino)-phenyl]-1-(tert-butyloxycarbonyl)-pyrrolidine To a solution of 4-tert-butyl-2-methoxy-benzoic acid (0.05 g) in DMF (1.5 mL) at room temperature, was added in order, 1-ethyl-3-(3-dimethylaminopropyl)-carbodiimide hydrochloride (0.046 g), 1-hydroxy-benzotriazole (0.033 g) and 15 min. later, (±)-2-(3-aminophenyl)-1-(tert-butyloxycarbonyl)-pyrrolidine (0.05 g). The reaction mixture was allowed to stir for 17 h and then poured into water. The aqueous mixture was extracted with ethyl acetate twice. The combined organic layer was washed with brine, dried (sodium sulfate) and evaporated in vacuo to afford an amber oil. Suction silica gel chromatography eluting with ethyl acetate in hexane (from 30% to 100%, in 10% increments) gave desired product as an amber solid (0.03 g).

$^1$H (400 MHz, CDCl$_3$): 1.22 and 1.46 (9H, 2 br. s); 1.36 (9H, s); 1.80–2.00 and 2.34 (4H, m); 3.60 (2H, 2 br. s); 4.07 (3H, s); 4.79 and 4.95 (1H, 2 br. s); 6.92 (1H, d); 7.02 (1H, s); 7.15 (1H, d); 7.27 (1H, t); 7.47 (1H, br. s); 7.55 (1H, br. s); 8.20 (1H, d); 9.78 (1H, br. s)

EXAMPLE 1

(±)-4-tert-Butyl-2-methoxy-N-(3-pyrrolidin-2-yl-phenyl)-benzamide, monohydroclhloride A solution of (±)-2-[3-(4-tert-butyl-2-methoxy-benzoylamino)-phenyl]-1-(tert-butyloxycarbonyl)-pyrrolidine (0.034 g) in methanol (3 mL) and 5M HCl (2 mL) was allowed to stir at room temperature for 18 h. Evaporation in vacuo gave the title compound as a colourless solid (0.029 g).

$^1$H (250 MHz, CD$_3$OD): 1.39 (9H, s); 2.10–2.60 (4H, m); 3.50 (2H, br. m); 4.08 (3H, s);4.67(1H, m);7.19(2H, m);7.29 (1H, d);7.49(1H, t);7.64(1H, d); 7.90 (1H, d); 8.02 (1H, br. s).

Using methods similar to those described for the preparation of Example 1, the following Examples were prepared.

EXAMPLE 2

(±)-4-tert-Butyl-2-methoxy-N-[3-(1-methylpiperidin-2-yl)phenyl]benzamide

PMR of the Free Base

δ$^1$H (250 MHz, CDCl$_3$): 1.36 (9H, s), 1.60–1.90 (5H, m), 2.05 (3H, s), 2.00–2.50 (2H, m), 2.81 (1H, d), 3.10 (1H, d), 4.10 (3H, s), 7.10 (1H, d), 7.15 (1H, dd), 7.30 (1H, t), 7.50 (1H, s), 7.70 (1H, d), 8.20 (1H, d), 9.80 (1H, br.s).

EXAMPLE 3

(±)-4-tert-Butyl-2-metboxy-N-[3-(1-methylpyrrolidin-2-yl)phenyl]benzamide

PMR of the Free Base

δ$^1$H (250 MHz, CDCl$_3$): 1.35 (9H, s), 1.60–2.40 (5H, m), 2.20 (3H, s), 3.05 (1H, t), 3.25 (1H, t), 4.07 (3H, s), 7.02 (1H, d), 7.05–7.20 (2H, m), 7.30 (1H, t), 7.54 (1H, s), 7.68 (1H, d), 8.20 (1H, d), 9.76 (1H, br.s).

Pharmacogical Data

1. Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 (SmithKline Beecham) bind to a novel receptor obtainable from rat forebrain tissue, as described in Patent WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active in this test. For example, the compound of Example 1 gave a pKi value greater than 7.

2. Mest Test

The maximal electroshock seizure threshold (MEST) test in rodents is particularly sensitive for detecting potential anticonvulsant properties[1]. In this model, anticonvulsant agents elevate the threshold to electrically-induced seizures whilst proconvulsants lower the seizure threshold.

Method

Mice (naive, male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

The percentage increase or decrease in $CC_{50}$ for each group compared to the control is calculated.

Studies are carried out using a Hugo Sachs Electronik Constant Current Shock Generator with totally variable control of shock level from 0 to 300 mA and steps of 2 mA are usually used.

Drugs are suspended in 1% methyl cellulose.

REFERENCES

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F. (1949). J. Pharmacol. exp. Ther., 96, 99–113

Results

Compounds of this invention dosed by the oral route as a suspension in methyl cellulose and tested one hour post dosing showed an increase in seizure threshold. For example, the compound of Example 1 gave a 53% increase at 10 mg/kg po.

What is claimed is:

1. A compound of formula (I) or pharmaceutically acceptable salt thereof:

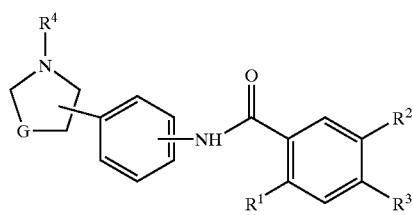

(I)

where

G is a methylene or ethylene linkage;

$R^1$ is hydrogen, $C_{1-6}$ alkylO—;

$R^2$ is hydrogen, halogen, CN, $N_3$, trifluoromethyldiazirinyl, $CF_3$, $CF_3O$—, $CF_3S$—, $CF_3CO$—, $C_{1-6}$alkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl and substituted benzoyl, phenyl-$C_{1-4}$alkyl-, $C_{1-6}$alkylSO$_2$—, ($C_{1-4}$alkyl)$_2$NSO$_2$— or ($C_{1-4}$alkyl)NHSO$_2$—;

$R^3$ is hydrogen, halogen, CN, $N_3$, trifluoromethyldiazirinyl, $C_{1-6}$ alkylO—, $C_{1-6}$ alkylS—, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO$—, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, or —NR$^5$R$^6$ where R$^5$ is hydrogen or $C_{1-4}$ alkyl, and $R^6$ is hydrogen, $C_{1-4}$alkyl, —CHO, —CO$_2$C$_{1-4}$alkyl or —COC$_{1-4}$alkyl;

$R^4$ is hydrogen, $C_{1-6}$ alkyl, $C_{1-6}$ alkenyl, or $C_{1-6}$ alkynyl.

2. A compound according to claim 1 which is a (2-pyrrolidinyl-phenyl)-benzamide or a (2-piperidin-yl-phenyl)-benzamide.

3. A compound according to claim 1 selected from the group consisting of:

(±)-4-tert-Butyl-2-methoxy-N-[3-(1-methylpiperidin-2-yl)phenyl]benzamide;

(±)-4-tert-Butyl-2-methoxy-N-(3-pyrrolidin-2-yl-phenyl)-benzamide, monohydrochloride; and (±)-4-tert-Butyl-2-methoxy-N-[3-(1-methylpyrrolidin-2-yl)phenyl]benzamide.

4. A pharmaceutical composition for use in the treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) which comprises a compound according to claim 1 and a pharmaceutically acceptable carrier.

5. A method of treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) comprising administering to the sufferer in need thereof an effective or prophylactic amount of a compound according to claim 1.

6. A pharmaceutical composition containing a compound of claim 1, or a pharmaceutically acceptable salt or solvate thereof, and a pharmaceutically acceptable carrier.

7. A process for the preparation of compounds of formula (I), which comprises reacting a compound of formula (II)

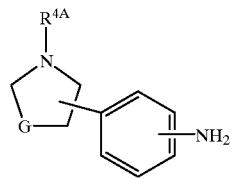

(II)

where

G is as defined for formula (I) and $R^{4A}$ is $R^4$ as defined for formula (I) or a group convertible to $R^4$ or a protecting group with a compound of formula (III)

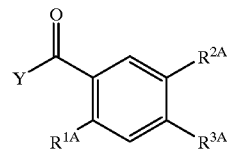

(III)

where Y is Cl or other halogen or OH, and $R^{1A}$, $R^{2A}$, and $R^3A$ are respectively $R^1$, $R^2$, and $R^3$ as defined for formula (I) or groups convertible to $R^1$, $R^2$, and $R^3$, and where required converting a $R^{1A}$, $R^{2A}$, $R^{3A}$ or $R^{4A}$ group to a $R^1$, $R^2$, $R^3$ or $R^4$ group, converting one $R^1$, $R^2$, $R^3$ or $R^4$ group to another $R^1$, $R^2$, $R^3$ or $R^4$ group, converting a hydrochloride salt product to the free base or another pharmaceutically acceptable salt, or converting a free base product to a pharmaceutically acceptable salt.

* * * * *